US00PP17213P2

(12) United States Plant Patent
Keogh

(10) Patent No.: US PP17,213 P2
(45) Date of Patent: Nov. 14, 2006

(54) ***CUPHEA* PLANT NAMED 'FLAMENCO RUMBA'**

(50) Latin Name: *Cuphea llavea×procumbens*
Varietal Denomination: FLAMENCO RUMBA

(76) Inventor: Terry Keogh, 209 Bunker Road, Victoria Point, Queensland (AU), 4165

( * ) Notice: Subject to any disclaimer, the term of this patent is extended or adjusted under 35 U.S.C. 154(b) by 0 days.

(21) Appl. No.: 11/334,122

(22) Filed: Jan. 17, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para

(57) ABSTRACT

A new cultivar of *Cuphea* named 'FLAMENCO RUMBA' that is characterized by open upright habit, dark yellow-green foliage, and large light red flowers that bloom continuously through spring, summer and fall. In combination these traits set 'FLAMENCO RUMBA' apart from all other existing varieties of *Cuphea* known to the inventor.

2 Drawing Sheets

Genus: *Cuphea*. Species: *llavea×procumbens*.
Denomination: 'FLAMENCO RUMBA'.

BACKGROUND OF THE INVENTION

The present invention relates to a new and distinct cultivar of *Cuphea* that is grown for use as an annual plant for container or for use as a perennial plant for the landscape in frost-free regions. The new cultivar is known botanically as *Cuphea llavea×procumbens* and will be referred to hereinafter by the cultivar name 'FLAMENCO RUMBA'.

The new *Cuphea* cultivar 'FLAMENCO RUMBA' is a hybrid plant that resulted from the induced cross-pollination conducted by the inventor in June 2001 at the inventor's nursery in Brisbane, Queensland, Australia. 'FLAMENCO RUMBA' was selected by the inventor in December 2003 based on light red flowers and open upright habit.

The inventor cross-pollinated an individual plant of the seed parent, *Cuphea llavea* 'Tiny Mice' (unpatented) and an individual plant of the pollen parent *Cuphea procumbens* (species, not a cultivar, unpatented). Observing that the resulting seedlings exhibited a range of flower colors and flower shapes, the inventor set aside several hundred of these seedlings for further growth trials in order to select the most promising combination of uniqueness of flower shape, flower color, and compactness of plant habit. Three, individual and distinct clones were selected from the seedling population by the inventor, in 2003. One selection constitutes the present invention, 'FLAMENCO RUMBA'. The other two selections are the subject of the inventor's co-pending applications, 'FLAMENCO TANGO' U.S. patent application Ser. No. 11/334,620 and 'FLAMENCO SAMBA' U.S. patent application Ser. No. 11/334,128.

'FLAMENCO RUMBA' exhibits open upright habit, large hairy flower buds, large light red flowers, and dark yellow-green foliage. Propagation is accomplished using vegetative cuttings. The closest comparison plant known to the inventor is the inventor's co-pending variety 'FLAMENCO SAMBA', which exhibits dark red flowers and dense upright plant habit. 'FLAMENCO RUMBA' is distinguishable from the comparison plant by light red flowers and open upright habit.

The new cultivar 'FLAMENCO RUMBA' is distinguishable from the seed parent by flower color, and lobes on an individual flower. The seed parent 'Tiny Mice' bears small orange flowers that individually exhibit two identical, fused lobes, whereas 'FLAMENCO RUMBA' bears light red flowers that individually exhibit six sub-equal lobes. 'FLAMENCO RUMBA' is distinguishable from the pollen parent by flower color and plant habit. *Cuphea procumbens* exhibits a spreading habit and bears purple flowers, whereas 'FLAMENCO RUMBA' exhibits an upright open habit and bears light red flowers.

The first asexual propagation was accomplished by the inventor in 2003 at the inventor's nursery in Brisbane, Australia. The method of propagation used was vegetative cuttings. Since that time, the distinguishing characteristics of 'FLAMENCO RUMBA' have been determined stable and reproduced true to type in successive generations of asexual reproduction.

SUMMARY OF THE INVENTION

The following represent the distinguishing characteristics of the new *Cuphea* cultivar 'FLAMENCO RUMBA'. In combination these traits set 'FLAMENCO RUMBA' apart from all other existing varieties of *Cuphea* known to the inventor. 'FLAMENCO RUMBA' has not been tested under all possible conditions and phenotypic differences may be observed with variations in environmental, climatic, and cultural conditions, however, without any variance in genotype.

1. *Cuphea llavea×procumbens* 'FLAMENCO RUMBA' exhibits large light red flowers.
2. The flowers of *Cuphea llavea×procumbens* 'FLAMENCO RUMBA' bloom continuously throughout spring, summer and fall.
3. *Cuphea llavea×procumbens* 'FLAMENCO RUMBA' is an annual plant for container, or a perennial plant in frost-free regions.

4. *Cuphea llavea×procumbens* 'FLAMENCO RUMBA' is readily propagated using vegetative cuttings.
5. *Cuphea llavea×procumbens* 'FLAMENCO RUMBA' exhibits open upright habit.
6. *Cuphea llavea×procumbens* 'FLAMENCO RUMBA' exhibits large hairy flower buds.
7. *Cuphea llavea×procumbens* 'FLAMENCO RUMBA' is recommended for use in hanging basket, window box, clay container, and as a border plant for the landscape.
8. *Cuphea llavea×procumbens* 'FLAMENCO RUMBA' exhibits dark yellow-green foliage.
9. *Cuphea llavea×procumbens* 'FLAMENCO RUMBA' is hardy to USDA Zone 10.
10. *Cuphea llavea×procumbens* 'FLAMENCO RUMBA' is 40 cm in height and 44 cm in width at maturity.

BRIEF DESCRIPTION OF THE DRAWINGS

The accompanying color drawings illustrate the overall appearance of the new *Cuphea* variety 'FLAMENCO RUMBA' showing the colors as true as it is reasonably possible to obtain in colored reproductions of this type. Colors in the drawings may differ from the color values cited in the detailed botanical description, which accurately describe the actual colors of the new variety 'FLAMENCO RUMBA'.

The drawing labeled

The drawing labeled

Figure 1:
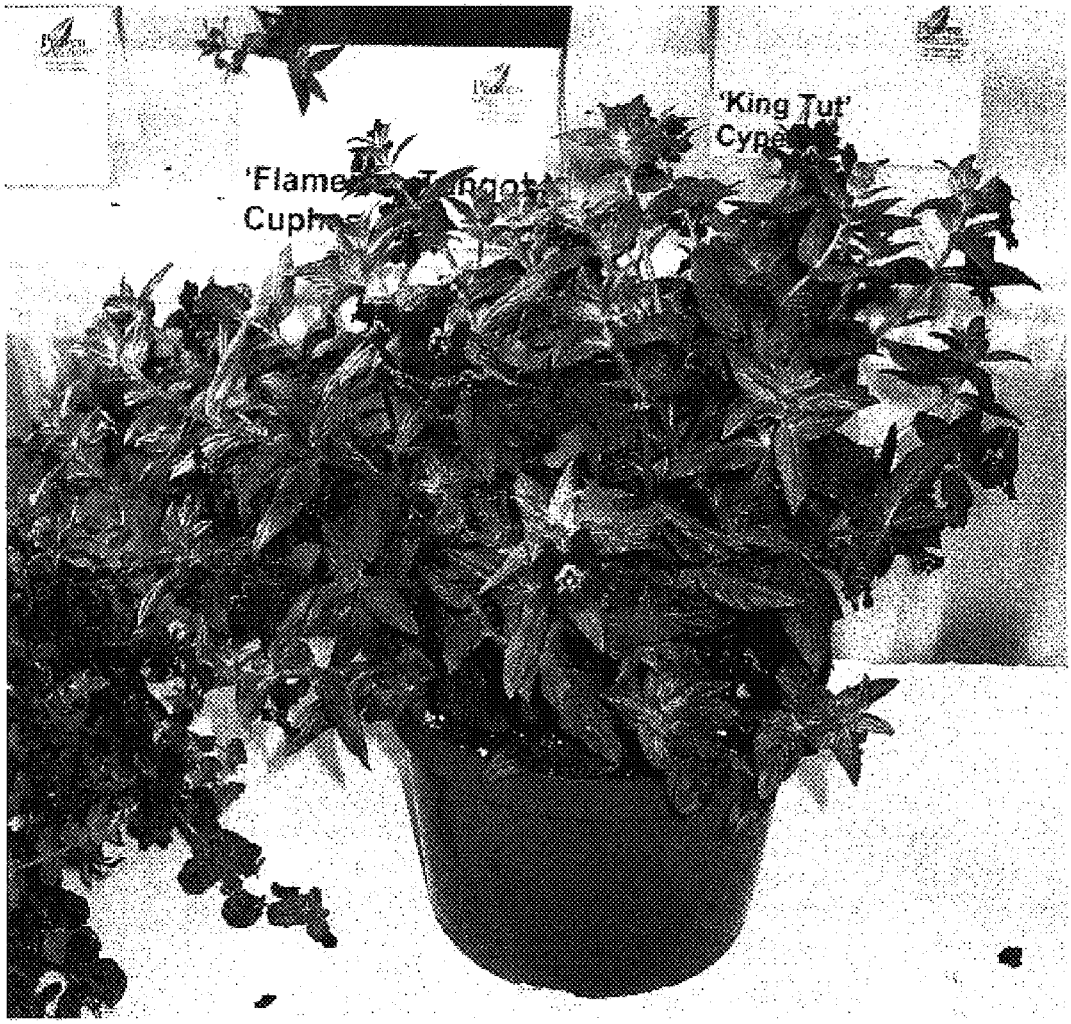
FIG. 1 depicts an entire plant in bloom from a side perspective.
Figure 2:
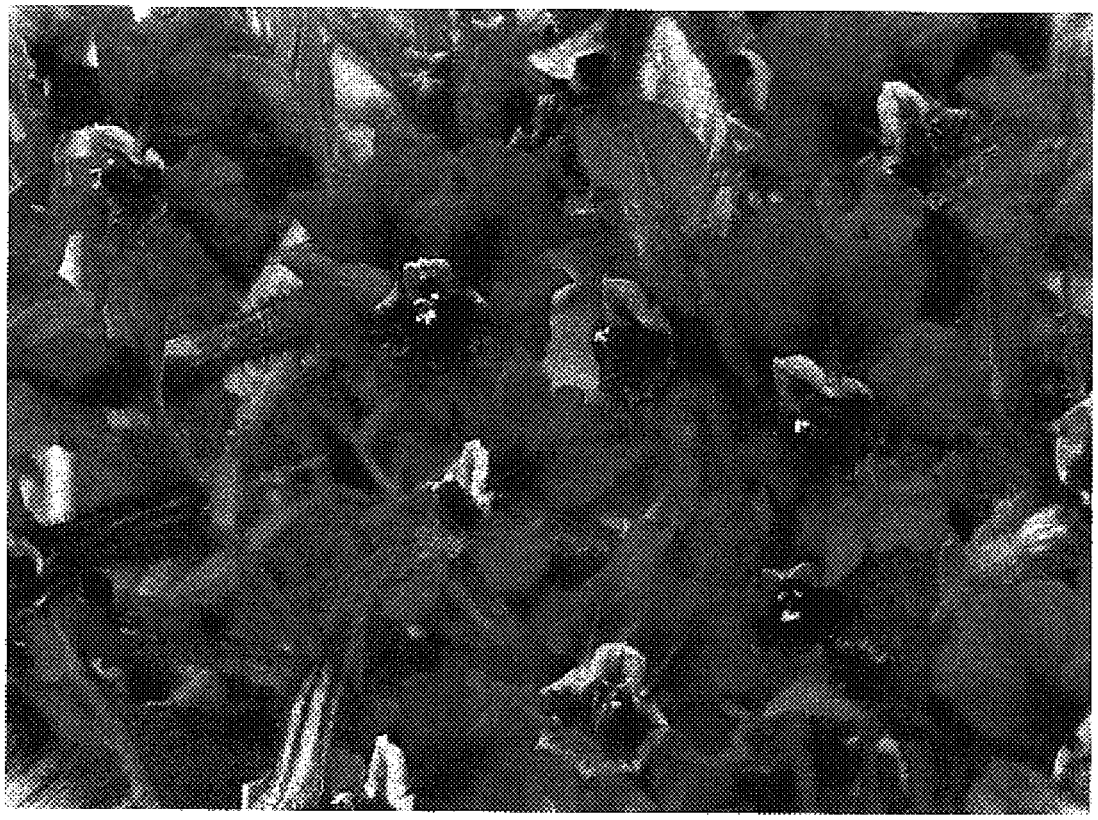
FIG. 2 depicts a close-up view of flower and bud.

All drawings are made using conventional techniques and although foliage colors may appear different from actual colors due to light reflectance, they are as accurate as possible by conventional photography.

BOTANICAL DESCRIPTION OF THE PLANT

The following is a detailed description of the *Cuphea* cultivar named 'FLAMENCO RUMBA'. Data was collected and compiled in Arroyo Grande, Calif. from 2-liter container plants that were 12-months-old at the time. Color determinations are in accordance with the 2001 Royal Horticultural Society Colour Chart except where general color terms of ordinary dictionary signficance are used. The growing requirements are similar to the species.

Botanical classification: *Cuphea llavea×procumbens* 'FLAMENCO RUMBA'.
Genus: *Cuphea.*
Plant species: *llavea×procumbens*.
Denomination: FLAMENCO RUMBA.
Common name: *Cuphea.*
Suggested uses: Recommended for use in hanging basket, window box, clay container, and as a border plant in the landscape.
Plant parentage: *Cuphea llavea×procumbens* 'FLAMENCO RUMBA' is a hybrid plant that resulted from the induced cross-pollination of the following parent plants:
*Seed parent.*—An individual *Cuphea llavea* 'Tiny Mice'.
*Pollen parent.*—An individual *Cuphea procumbens.*
Plant type: An annual for use in container and a perennial for the landscape in frost-free regions.
Commercial category: Annual bedding plant; perrennial in frost free zones.
Recommended commercial container size: 2-liter commercial container.
Plant vigor: Moderate.
Plant habit: Open uprightt.
Plant dimension (at maturity): 40 cm in height and 44 cm in width.
Plant dimensions (in a 2-liter container): 27 cm in height and 30 cm in width.
Plant hardiness: Hardy to USDA Zone 10.
Plant propagation: Readily propagated using vegetative cuttings.
Root system: Fleshy root system.
Cultural requirements: Plant in full sun using rich, well-draining potting soil, with regular watering.
Time to initiate rooting: 4–6 weeks are needed to produce roots on an initial cutting.
Crop time: 9–12 months are needed to produce a finished 2-liter container from a rooted cutting.
Seasonal interest: Large light red flowers that bloom continuously throughout spring, summer and fall.
Disease and pests: None known to the inventor.
Special growing considerations: Use a hight nitrogen fertilizer once a season and a water-soluble fertilizer twice a month.
Stem:
*Basal trunk.*—One in number.
*Basal trunk color.*—145A.
*Basal trunk surface.*—Pubescent.
*Basal trunk shape.*—Cylindrical.
*Basal trunk diameter.*—0.50 cm.
*Basal trunk height.*—1.50 cm.
*Stem surface.*—Villous.
*Color of villi.*—166B and 165D.
*Stem shape.*—Cylindrical.
*Stem color.*—145A.
*Stem diameter.*—3 mm.
*Stem length.*—5 cm to 12 cm.
*Branching pattern.*—Divergent.
Foliage:
*Leaf type.*—Evergreen.
Internode length: 1 cm to 3.50 cm.
*Leaf arrangement.*—Opposite.
*Leaf division.*—Simple.
*Leaf quantity.*—18 to 20 leaves on an individual stem.
*Leaf shape.*—Ovate.
*Leaf base.*—Rounded.
*Leaf apex.*—Acute apex.
*Leaf venation pattern.*—Pinnate.
*Vein color* (*abaxial and adaxial surfaces*).—147D.
*Leaf surface* (*adaxial*).—Villose.
*Leaf surface* (*abaxial*).—Villous.
*Leaf attachment.*—Both sessile and petiolate.
*Petiole dimensions.*—4 mm in length and 1.75 mm in width.
*Petiole shape.*—Cylindrical.
*Petiole color.*—138B.
*Petiole surface.*—Glabrous.
*Stipules.*—None observed.
*Leaf margin.*—Minutely toothed.
*Leaf color* (*adaxial surface*).—147A.
*Leaf color* (*abaxial surface*).—147B.
*Leaf length.*—1.50 cm to 4.50 cm.
*Leaf width.*—0.50 cm to 2 cm.
*Foliar fragrance.*—None observed.

Flower:

*Blooming season.*—Continuously throughout spring, summer and fall.
*Inflorescence type.*—Raceme.
*Quantity of flowers.*—6–8 per raceme.
*Flower shape.*—Closest to salverform.
*Corolla.*—None observed.
*Hypanthium.*—Conspicuous.
*Flower aspect.*—Facing upward and outward.
*Flower color.*—43A, 41A, 77A, 63D and 147A all present on each flower.
*Flowers self-cleaning or persistent.*—Self-cleaning.
*Pedicel color.*—145A.
*Pedicel shape.*—Cylindrical.
*Pedicel length.*—6 mm.
*Pedicel width.*—1 mm.
*Pedicel surface.*—Villous.
*Flower bud shape.*—Cylindrical.
*Flower bud surface.*—Combination of villous and multicostate.
*Color of villi.*—156B.
*Flower bud texture.*—Viscidulous.
*Flower bud colors.*—43A and 63D, 147A at base.
*Flower bud apex.*—Closest to truncate, and enclosing 6 crumpled valvate lobes.
*Flower bud base.*—Combination of gibbous and oblique.
*Flower bud dimensions.*—2 cm in length and 0.50 cm in diameter.
*Flower diameter.*—3 cm.
*Flower depth.*—2.50 cm.
*Corolla tube diameter.*—0.50 cm.
*Corolla tube length.*—2 cm.
*Corolla tube color* (*ventral and dorsal surfaces*).—77B and 63D, 147A at base.
*Corolla tube shape.*—Tubular.
*Corolla tube apex.*—Flared apex.
*Corolla tube base.*—Combination of gibbous and oblique.
*Corolla tube surface* (*ventral and dorsal surfaces*).—Combination of villous and multicostate.
*Corolla tube texture.*—Viscidulous.
*Petals.*—Apetalous.

Calyx (sepals form valvate lobes):

*Valvate lobe number.*—6 sub-equal valvate lobes; 4 small lobes and 2 large lobes.
*Valvate lobes attachment.*—At summit of hypanthium.
*Valvate lobe arrangement.*—Rotate.
*Large valvate lobe dimensions.*—1.50 cm in width and 1.60 cm in length.
*Small valvate lobe dimensions.*—0.65 cm in width and 0.75 cm in length.
*Valvate lobe color* (*adaxial and abaxial surfaces*).—Colors 43A, 41A, and 77A.
*Valvate lobe texture* (*small and large lobe*).—Delicate.
*Valvate lobe surfaces* (*adaxial and abaxial surfaces*).—Rugose.
*Valvate lobe appearance.*—Irridescent.
*Valvate lobe shape.*—2 orbicular lobes and 4 obovate lobes.
*Valvate lobe apex.*—Obtuse and rounded.
*Valvate lobe base.*—Cuneate and rounded.
*Valvate lobe margins.*—Sinuous.
*Valvate lobes unfused or fused.*—Unfused.

Flower fragrance: None observed.

Reproductive organs:

*Stamens.*—10 in number semi-exserted and adnate to ventral surface.
*Color of stamens.*—77D.
*Stamen demensions.*—5 stamens are 0.50 cm in length and 5 stamens are 0.75 cm in length.
*Anthers.*—The 5 long stamens are tufted with dense violet hairs and the 5 short stamens exhibit anthers.
*Color of hairs.*—84D.
*Anther dimensions.*—1 mm in length and 0.75 mm in width.
*Anther color.*—84D.
*Amount of pollen.*—Minimal amount.
*Pollen color.*—84D.
*Pistil.*—One in number.
*Pistil length.*—2.50 cm.
*Pistil shape.*—Filament.
*Pistil surface.*—Pubescent.
*Pistil color.*—Individual colors 145C and 77B are present.
*Stigma color.*—77B.
*Stigma shape.*—Bifid.
*Stigma dimensions.*—0.25 mm in length and 0.25 mm in diameter.
*Ovary position.*—Superior.
*Ovary shape.*—Ovoid.
*Ovary color.*—145C.
*Ovary surface.*—Rugose.
*Ovary dimensions.*—0.50 cm in width and 0.55 cm in height.
*Fruit.*—Dry, dehiscent, ovoid capsule.
*Capsule.*—3 locules, splitting between each.
*Color* (*prior to splitting*).—Between 152A and 152D.
*Dimensions* (*prior to splitting*).—4 mm in diameter, 5 mm in length.

Seed:

*Number of seeds.*—35 approximately.
*Seed shape.*—Globose.
*Seed surface.*—Glabrous.
*Seed color.*—N144D.
*Seed dimensions.*—0.50 mm in diameter and 0.50 mm in height.

It is claimed:

1. A new and distinct variety of *Cuphea* plant named 'FLAMENCO RUMBA' as described and illustrated herein.

* * * * *